United States Patent
Fu et al.

(10) Patent No.: US 7,187,792 B2
(45) Date of Patent: Mar. 6, 2007

(54) APPARATUS AND METHOD FOR DETERMINING MEASURE OF SIMILARITY BETWEEN IMAGES

(75) Inventors: Dongshan Fu, Santa Clara, CA (US); Gopinath Kuduvalli, San Jose, CA (US)

(73) Assignee: Accuray, Inc., Sunnyvale, CA (US)

( * ) Notice: Subject to any disclaimer, the term of this patent is extended or adjusted under 35 U.S.C. 154(b) by 728 days.

(21) Appl. No.: 10/652,717

(22) Filed: Aug. 29, 2003

(65) Prior Publication Data

US 2005/0049477 A1   Mar. 3, 2005

(51) Int. Cl.
*G06K 9/00*   (2006.01)

(52) U.S. Cl. ........................... 382/128; 382/132

(58) Field of Classification Search ................ 382/128, 382/129, 130, 131, 132–134; 378/28, 46, 378/63, 90, 92, 98, 98.4, 98.6, 98.9, 101, 378/140, 207; 600/302, 407, 426, 427; 250/491.1, 250/492.1
See application file for complete search history.

(56) References Cited

U.S. PATENT DOCUMENTS

| | | | | |
|---|---|---|---|---|
| 5,117,829 A | * | 6/1992 | Miller et al. | 600/427 |
| 5,901,199 A | * | 5/1999 | Murphy et al. | 378/65 |
| 6,470,207 B1 | * | 10/2002 | Simon et al. | 600/426 |
| 2004/0092815 A1 | | 5/2004 | Schweikard et al. | |
| 2004/0267113 A1 | | 12/2004 | Thomson | |

OTHER PUBLICATIONS

Graeme P. Penny et al., A Comparison of Similarity Measures for Use in 2-D-3-D Medical Image Registration, IEEE Transactions on Medical Imaging, vol. 17, No. 4, Aug. 1998.

Graeme P. Penney, et al., "Validation of a two- to three-dimensional registration algorithm for aligning preoperative CT images and intraoperative fluoroscopy images," Med. Phys. 28(6), 1024-1032, Jun. 2001.

D. Sarrut, et al., "Patient positioning in radiotherapy by registration of 2D portal to 3D CT images by a contend-based research with similarity measures," CARS 2000, 707-712.

Martin J. Murphy, "An automatic six-degree-of-freedom image registration algorithm for image-guided frameless stereotaxic radiosurgery," Med. Phys. 24(6), 857-866, Jun. 1997.

* cited by examiner

*Primary Examiner*—Matthew C. Bella
*Assistant Examiner*—Abolfazi Tabatabai
(74) *Attorney, Agent, or Firm*—Blakely, Sokoloff, Taylor & Zafman LLP

(57) ABSTRACT

A method and system is presented in image-guided radiosurgery for determining the measure of similarity of two digital images, for example a 2D x-ray image and a 2D DRR synthesized from 3D scan data. A two-dimensional array of pixel values of a difference image is formed by subtracting each pixel value of the second image from the corresponding pixel value of the first image. The pattern intensity function is constructed by taking the summation of asymptotic functions of the gradients of the difference image. The neighborhood R is defined so as to allow the gradients of the difference image to be considered in at least four directions.

17 Claims, 3 Drawing Sheets

APPARATUS AND METHOD FOR DETERMINING MEASURE OF SIMILARITY BETWEEN IMAGES

FIELD OF THE INVENTION

The present invention relates to an apparatus and method for determining the measure of similarity of two images.

BACKGROUND

Radiosurgery is useful for treating tumors and other lesions by delivering a prescribed high dose of high-energy radiation to the target area while minimizing radiation exposure to the surrounding tissue. In radiosurgery, precisely focused beams of radiation (e.g. very intense x-ray beams) are delivered to a target region in order to destroy tumors or to treat the tumor for other purposes. The goal is to apply a lethal or other desired amount of radiation to one or more tumors, without damaging the surrounding healthy tissue.

Conventional radiosurgery uses a rigid and invasive stereotactic frame to immobilize the patient prior to diagnostic CT or MRI scanning. The treatment planning is then conducted from the diagnostic images. The treatment planning software determines the number, intensity, and direction of the radiosurgical beams that should be cross-fired at the target, in order to ensure that a sufficient dose is administered throughout the tumor so as to destroy it, without damaging adjacent healthy tissue. Immobilization of patient is necessary in order to maintain the spatial relationship between the target and the radiation source that ensures accurate dose delivery. The frame is fixed on the patient during the whole treatment process, causing pain and inconvenience to the patient.

Image-guided radiosurgery allows the elimination of such invasive frame fixation, during treatment. In an image-guided radiosurgical process, the patient position and the relative alignment of the radiation beam with respect to the patient target is continuously adjusted. In order to ensure the delivery of the correct dose of radiation to the correct location, the patient (and target) position during treatment needs to be detected. This is accomplished by registering the x-ray image acquired at the treatment time with the diagnostic 3D scan data (e.g., CT, MRI, ultrasound, or PET scan data) obtained pre-operatively at the time of treatment planning. In the field of medical image registration, this problem is categorized as a 2D/3D registration.

In the 2D/3D registration process, similarity measures are useful for comparing the image intensities in the x-ray images and the DRR images, so that the change in patient position (and thus in target region position) that has occurred between the diagnostic scanning and the taking of real-time images can be accurately detected. Image-guided radiosurgery requires precise and fast positioning of the target at the treatment time. In practice, the accuracy should be below 1 mm, and the computation time should be on the order of a few seconds. Unfortunately, it is difficult to meet both requirements simultaneously. In order to optimize the 2D/3D registration process in image-guided radiosurgery, it is necessary to provide an accurate, robust, and efficient similarity measure method and system.

SUMMARY OF THE INVENTION

The present invention is directed to an improved method and system for comparing the measure of similarity of two digital images, in image-guided radiosurgery. The method is based on pattern intensity, and provides a more robust, accurate, and efficient solution to the 2D/3D medical image registration problem, as compared to other methods known and used in the art.

The present invention features a method in image-guided radiosurgery for determining the measure of similarity of a first image and a second image of an object. Preferably, the first image is a real-time 2D x-ray image, and the second image is an artificially synthesized DRR, constructed from previously generated 3D scans.

The method includes forming a difference image by subtracting the corresponding pixel values of the second (DRR) image from each pixel value of the first, "live," x-ray image. The method further includes applying upon each pixel of the difference image a pattern intensity function, the pattern intensity function being an asymptotic function of the gradients of the difference image.

The mathematical formulation of pattern intensity function is given by:

$$\sum_{i,j}\sum_{k,l \in R} \frac{\sigma^2}{\sigma^2 + (I_{dif}(i,j) - I_{dif}(i+k, j+l))^2},$$

where $I_{dif}(i,j)$ represents the array of pixel values for the difference image, where $\sigma$ is a constant, and where R is a neighborhood that uses the pixel (i,j) as a center point.

In a preferred embodiment of the invention, the neighborhood R is defined so that the gradients of the difference image can be considered in at least four directions. In an exemplary embodiment, the four directions are: substantially horizontal; substantially vertical; about 45 degrees; and about −45 degrees.

The present invention features a system for determining the measure of similarity of a 2D x-ray image of an object and a 2D DRR of the object generated from previously obtained 3D scan data. Typically, the x-ray image and the DRR are discretized digital images, which are characterized by a first and second 2D array of pixel values. The system includes means for generating 3D scan data of the target, for example a CT scanner, an MRI system, or a PET system. A radiation source (typically an x-ray source) is provided for generating at least one imaging beam. Imaging means are provided for generating a 2D radiographic image of the target in near real time, by directing the imaging beam towards and through the target from a known location and angle and at a known intensity, and detecting the imaging beam after the beam has passed through the target.

The system includes a controller, which contains software for generating a set of DRR images of the target, using the known location, angle, and intensity of the imaging beam. The controller also includes software for determining the measure of similarity between the 2D x-ray image and the 2D DRR, by subtracting each pixel value of the second image from a corresponding pixel value of the first image to form a difference image, and then applying upon each pixel of the difference image to form a pattern intensity function. The pattern intensity function is an asymptotic function of the gradients of the difference image, and permits the pixel values within a neighborhood R defined about each pixel in the difference image to be considered. The gradients are defined over at least four directions, as discussed above.

DETAILED DESCRIPTION

The present invention is directed to a similarity measure, based on pattern intensity, for use in 2D/3D medical image registration. Similarity measures are used to compare two images, each of which have been generated using different modalities (e.g., CT versus x-rays), so that information from one image can be registered onto the other. Similarity measures are useful in procedures such as the 2D/3D medical image registration procedures in image-guided radiosurgery. The similarity measure method and system disclosed in the present invention allows for selected phases of the 2D/3D registration process in image-guided radiosurgery to be carried out in a more robust, efficient, and powerful manner, as compared to processes carried out using other similarity measures known and used in the art.

As explained in the background section, 2D/3D registration is necessary in order to correct patient position and properly align the radiosurgical beam relative to the target. The x-ray image acquired at treatment time is registered with the 3D scan obtained at the time of treatment planning. A CT scan is most frequently used for the 3D scan; however, other 3D scanning methods, such as MRI, ultrasound or PET scanning, may also be used. The 3D data is used as the reference to determine the patient position change during treatment. For this purpose, 2D reference images are reconstructed from the 3D scan data. Typically, digitally reconstructed radiographs (DRRs) need to be generated from 3D CT data and are used as the 2D reference images.

Figure 1:
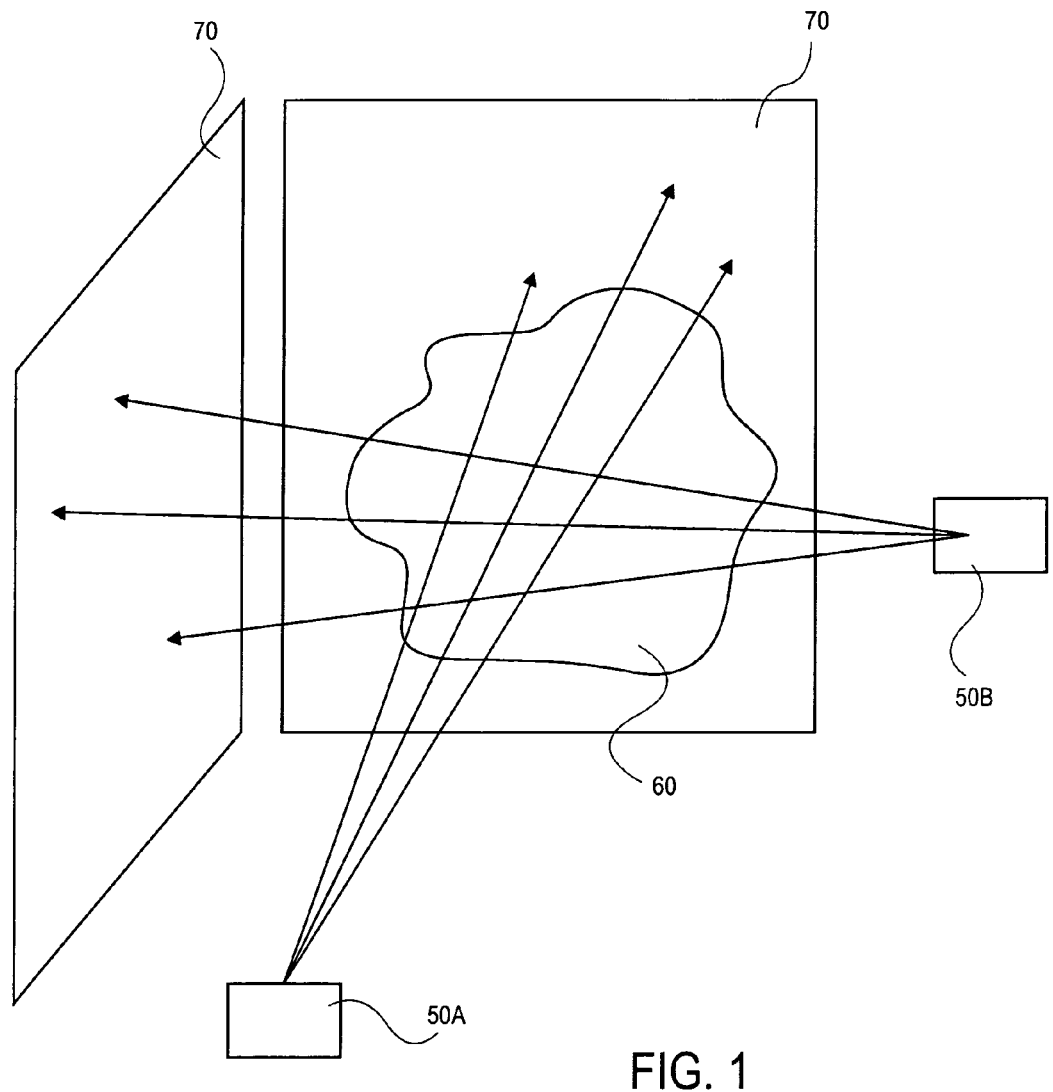
FIG. 1 illustrates the generation of 2D DRRs from 3D CT scan data of a treatment target within an anatomical region of a patient.
Figure 2:
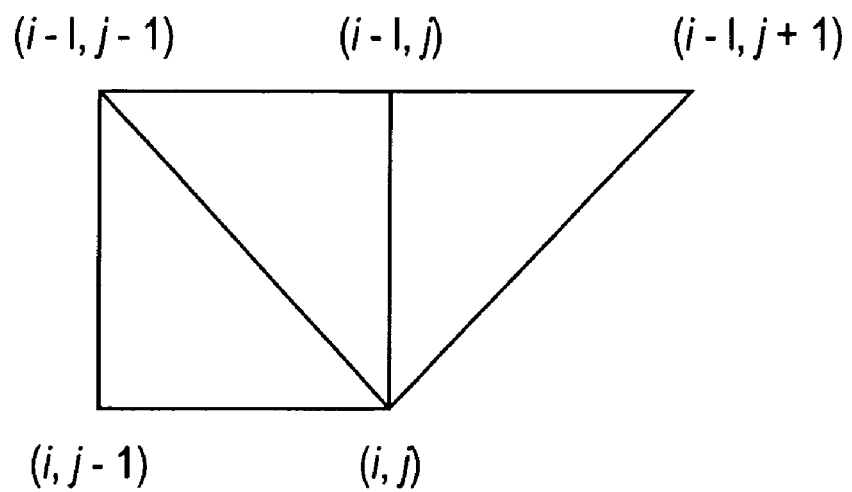
FIG. 2 schematically illustrates the neighborhood for calculating pattern intensity, in one embodiment of the present invention.

FIG. 1 illustrates the generation of 2D DRRs from 3D CT scan data of a treatment target within an anatomical region of a patient. In FIG. 1, the volumetric 3D CT image of the target is schematically referred to using reference numeral 60. The DRRs 65A and 65B, shown in FIG. 2, are artificial, synthesized 2D images that represent the radiographic image of the target that would be obtained if imaging beams were used having the same intensity, position and angle as the beams used to generate the real time x-ray projection images, and if the target were positioned in accordance with the 3D CT scan data. The reference numerals 50A and 50B illustrate the hypothetical positions and angles from which the imaging beams would be directed through a target positioned in accordance with the CT volumetric image 60 of the target.

Typically, DRRs are generated by casting hypothetical beams or rays through the CT volumetric image of the target. Each ray goes through a number of voxels of the 3D CT image 60. By integrating the CT numbers for these voxels along each ray, and projecting onto an imaging plane (shown as 70A and 70B, respectively, in FIG. 2), the resultant image would emulate the radiograph that would be obtained by passing rays from hypothetical locations (50A and 50B, respectively) through a target positioned in accordance with the volumetric 3D image 60. Ray tracing algorithms, known in the art, are generally used to generate DRRs.

Applications such as image-guided radiosurgery require that the comparison between the DRRs (that contain the 3D CT scan information) and the real-time x-ray images, and consequent adjustment of the position of the x-ray source, be made very rapidly and accurately. In practice, the accuracy should be below 1 mm, and the computation time should be on the order of a few seconds. Unfortunately, it is difficult to meet both requirements simultaneously, because of several reasons. First, the two different modality images, i.e. CT scan images and x-ray images, have different spatial resolution and image quality. Generally, x-ray image resolution and quality are superior to the resolution and quality of DRR images, which are only synthesized images. Typically, some structures in the DRR may appear more blurred (especially normal to the CT slice plane), compared to the x-ray image. Ideally, an optimal similarity measure for a 2D/3D registration process should allow for an accurate registration to be achieved, despite such differences.

Second, DRR generation relies on a proper attenuation model. Because attenuation is proportional to the mass intensity of the target volume through which the beam passes, the exact relationship between the traversed mass intensity and the CT image intensity needs to be known, in order to obtain an accurate modeling. Establishing this relationship is difficult, however, so the linear attenuation model is often used. As is known, the linear attenuation coefficient of a material is dependent on x-ray energy. CT machines and x-ray machines work at different effective energies, however. As a result, the attenuation coefficients measured by a CT scanner are different from the attenuation of a beam of x-rays passing through the target. The skeletal structures in DRR images cannot be reconstructed very well using the linear model, the DRRs being only synthetic x-ray projection images. At CT energies, the ratio of bone-to-soft-tissue attenuation is much lower than at x-ray radiographic energies. Thus, in a DRR produced from a 3D CT volume, the image contrast from soft tissue will be comparable with the image contrast from bone, reducing the clarity of bone details, for example.

Finally, x-ray images usually have a large image size (512×512). For better registration accuracy, it is desirable to use the full resolution image. Full resolution images are rarely used, in practice, however, because the resulting increase in computation time is excessive, and is incompatible with the requirements of image-guided radiosurgery.

Generally, similarity measure methods used in 2D/3D registration can be divided into two categories. The first method is based on image features. The image features could be anatomical edges or segmented objects. The registration accuracy depends on the accuracy of edge detection or object segmentation. The main advantage of this method is its fast computation. Feature-based similarity methods register on salient features that have been segmented from each image. They use a reduced amount of data, which makes the algorithms fast, once the segmentation has been undertaken. Because the full information content of the image is not used, however, the accuracy is sacrificed. Errors in the segmentation stage can lead to an error in the final registration.

The second method is based on image intensity content. Intensity-based methods compare the voxel and pixel values directly, using measures based on image statistics. The original images are used for registration. Usually, a good accuracy can be achieved. Although these methods require little or no segmentation, intensity-based methods are typically much slower. Because a long time computation is required, it is hard to apply intensity-based similarity measures to clinical practice.

In a co-pending patent application Ser. No. 10/652,786 a method and system for 2D/3D image registration is disclosed that uses a hierarchical and iterative framework for the registration algorithm, to achieve a higher accuracy with less computing time. The application Ser. No. 10/652,786 is owned by the assignee of the present application, and is hereby incorporated by reference in its entirety. In the application Ser. No. 10/652,786, a 2D/3D image registration procedure is disclosed that includes the steps of 1) performing a 3D multi-level matching to determine an initial estimate in-plane transformation parameters, 2) performing an initial 1-D search for each of a pair of out-of-plane rotation parameters, then 3) iteratively refining the in-plane parameters (x, y, θ) and the out-of-plane parameters (r, φ), until the parameters converge to a desired accuracy. The similarity measure methods disclosed in the present invention are designed to optimize the 2D/3D image registration procedure disclosed in the application Ser. No. 10/652,786.

The similarity measure method of the present invention is based on pattern intensity, and provides a powerful and efficient way to solve the 2D/3D image registration procedure, as disclosed in the application Ser. No. 10/652,786. In particular, the pattern intensity based method and system of the present invention is designed for the 1D search phase (for the out-of-plane parameters), and the iterative refining phases of the 2D/3D image registration procedure disclosed in the application Ser. No. 10/652,786.

For the 3D multi-level search phase, the "sum of absolute differences" (SAD) measure is used, which is a known, simple similarity measure. The SAD measure is widely used in medical image processing and video processing, in cases where the two images to be matched have high image quality. The main advantage of using SAD is its fast computation and its easy optimization in parallel computation. Its main disadvantage is that the solution is sensitive to image noise, artifacts and intensity difference between the live and DRR images. As a result, SAD is only used in the first search phase to get approximate results. SAD can be expressed as $$SAD = \sum_{i,j} |I_{Live}(i, j) - I_{DRR}(i, j)|,$$

where $I_{live}(i, j)$ represents the intensity of the "live" real-time x-ray image, and $I_{DRR}(i, j)$ represents the intensity of the reconstructed DRR image.

The pattern intensity similarity measure of the present invention is more accurate, and less sensitive to image noise, artifacts, and to the intensity difference between the images being compared. In the exemplary embodiment described in the following paragraphs, the first image is a 2D x-ray image of a radiosurgical treatment target, and the second image is a 2D DRR that is reconstructed from 3D CT scan data generated at the time of treatment planning. In a preferred embodiment, the two images are discretized, digital images, characterized by first and second 2D arrays of pixel values. The pixel arrays are equi-dimensional, i.e. the number of rows and columns of the first array is equal to the number of rows and columns of the second array. As well known, each pixel value of an image is a number representative of the intensity of the image at a unique corresponding 2D area element forming the image.

A difference image is formed from the real-time x-ray image and the DRR image, by subtracting the corresponding pixel values of the second image (the DRR image) from each pixel value of the first image (the real-time):

$$I_{dif}(i, j) = I_{Live}(i, j) - I_{DRR}(i, j),$$

where $I_{dif}(ij)$ represents the intensity or pixel value of the ij-th pixel of the difference image, $I_{live}(ij)$ represents the intensity or pixel value of the ij-th pixel of the live x-ray image; and $I_{DRR}(i,j)$ represents the intensity or pixel value of the ij-th pixel of the artificial DRR image.

A pattern intensity function is defined, which operates on the difference image. The pattern intensity function is expressed as an asymptotic function of the gradients of the difference image:

$$\sum_{i,j} \sum_{k,l \in R} \frac{\sigma^2}{\sigma^2 + (I_{dif}(i, j) - I_{dif}(i+k, j+l))^2}, \quad (1)$$

where σ is a weighting constant and R is a neighborhood that is defined using the pixel (i, j) as the center point. The form of the mathematical formulation results in the similarity measure tending to a maximum value, as the number of structures tend to zero, and the similarity measure asymptotically tending to zero, as the number of structures increase. Because of the asymptotic nature of the pattern intensity measure, large differences in intensity have the same effect on the measure, regardless of their magnitude. This makes the measure robust to large differences in pixel intensity.

The function is weighted by the weighting constant σ. The constant σ is used to weight the function, so that small deviations in intensity (caused by noise, by way of example) results in the measure remaining proximate to its maximum value. The sensitivity of the solution to the variation of X-ray image can be minimized by careful selection of this constant. The larger the weighting constant, the more stable the results become. However, the choice of the weighting constant is a tradeoff between stability and accuracy. If the value of the weighting constant is too large, the smaller details in the images cannot be reflected in the similarity measure. Based on experimentation, the empirical value of σ is determined to be in the range from about 4 to about 16, although other values of σ are also within the scope of the present invention.

The pattern intensity function considers a selected neighborhood for each pixel. In a preferred embodiment of the invention, illustrated in FIG. 2, the neighborhood R is defined such that the gradients in four directions are considered: horizontal, vertical, 45° diagonal and −45° diagonal. As shown in FIG. 2, in the horizontal direction, the (i, j−1)-th pixel is considered. In the vertical direction, the (i−1 j)-th pixel is considered. In the 45° diagonal direction, the (i−1, j+1)-th pixel is considered. In the −45° direction, the (i−1, j−1)-th pixel is considered.

Based on the definition of the neighborhood R as shown in FIG. 2, the pattern intensity expression is given as the sum below:

$$\sum_{i,j} \frac{\sigma^2}{\sigma^2 + (I_{dif}(i,j) - I_{dif}(i,j-1))^2} + \sum_{i,j} \frac{\sigma^2}{\sigma^2 + (I_{dif}(i,j) - I_{dif}(i-1,j))^2} + \sum_{i,j} \frac{\sigma^2}{\sigma^2 + (I_{dif}(i,j) - I_{dif}(i-1,j-1))^2} + \sum_{i,j} \frac{\sigma^2}{\sigma^2 + (I_{dif}(i,j) - I_{dif}(i-1,j+1))^2} \quad (2)$$

The formulation of the pattern intensity function, given in equation (2) above, provides a number of advantages over other known similarity measures, as discussed in paragraph 41 below.

Figure 3:
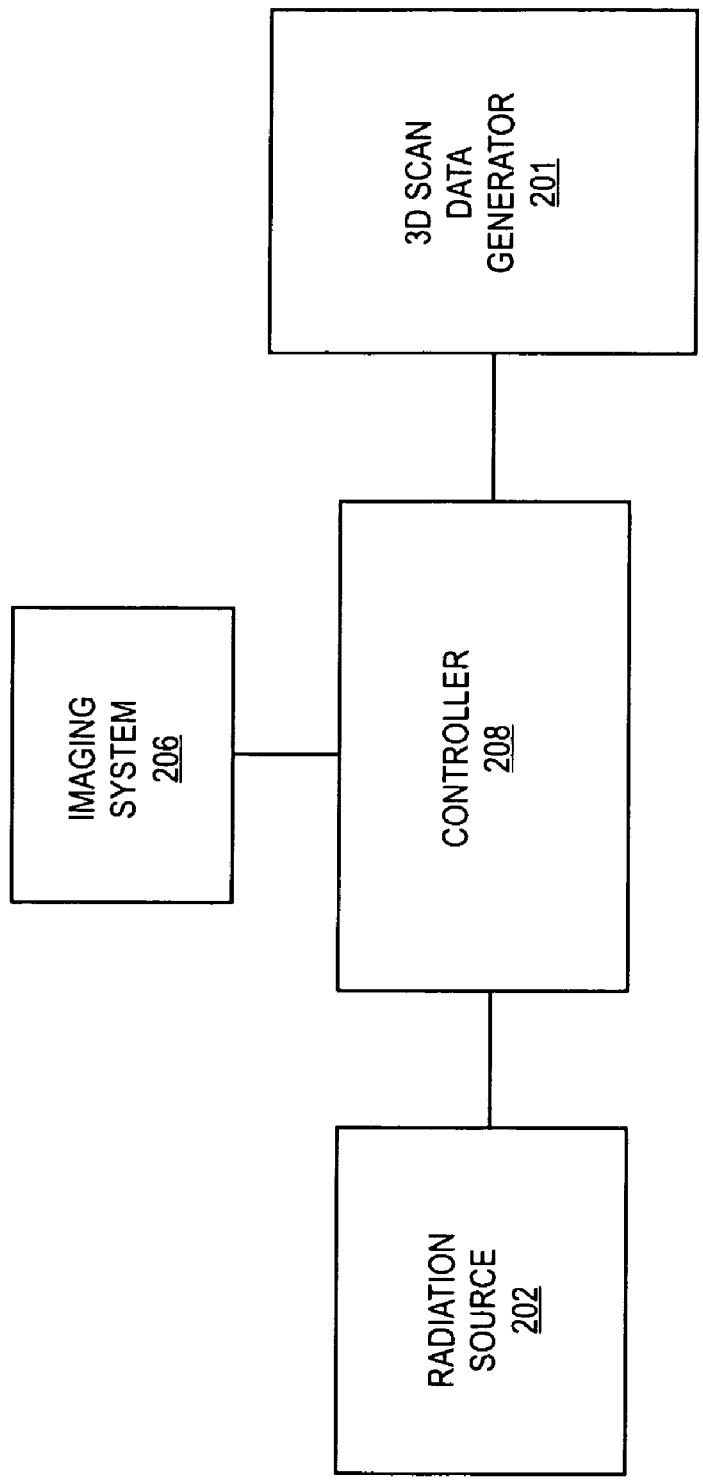
FIG. 3 illustrates a schematic block diagram of a system for determining the measure of similarity between an x-ray image of an object, and a synthesized DRR of the object, constructed in accordance with one embodiment of the present invention.

FIG. 3 schematically illustrates a system 200 for determining, during image-guided surgery, the measure of similarity between two images, constructed in accordance with one embodiment of the present invention. The present invention features a system for determining the measure of similarity of a 2D x-ray image of an object, and a 2D DRR of the object generated from previously obtained 3D scan data. Preferably, the x-ray image and the DRR are discretized digital images, which are characterized by a first and second 2D array of pixel values. The system includes a 3D scanner for generating 3D scan data of the target. The 3D scanner may include, but is not limited to, a CT scanner, an MRI system, an ultrasound system, and a PET system.

A radiation source 202 (typically an x-ray source) is provided for generating at least one imaging beam (typically an x-ray beam). An imaging system 206 is provided for generating a 2D radiographic image of the target in near real time, by directing the imaging beam towards and through the target from a known location and angle and at a known intensity, and detecting the imaging beam after the beam has passed through the target. The imaging system 206 is preferably an x-ray imaging system for generating a pair of orthogonal x-ray projection images of the target. The imaging system 206 preferably has a pair of x-ray sources for generating diagnostic imaging beams (having known positions, angles, and intensities), and a corresponding pair of x-ray image detectors which detect the beams after the beams have passed through the target.

The system includes a controller 208. The controller 208 includes software for generating a set of reconstructed 2D images (preferably DRRs) of the target, based on the 3D scan data from the 3D scanner 201, and the known intensity, location, and angle of the imaging beams. The controller also includes software for determining the measure of similarity between the 2D x-ray image and the 2D DRR, in a manner described above in paragraphs 28–36.

The pattern intensity similarity measure of the present invention provides a number of advantages over other methods known in the art. First, the difference image filters out the low frequency part that is basically the soft tissues and keeps the high frequency part that is mostly the skeletal structures. This feature makes the algorithm robust to some brightness intensity difference between live and DRR images. Second, because of the asymptotic nature of the pattern intensity function, the similarity measure is less affected by pixels whose intensity values deviate only slightly from its neighboring pixels. These kinds of pixels are thought to contain random noise, hence undesirable. Third, because the asymptotic function quickly approaches to zero when the variable increases, large intensity differences such as image artifacts have the same effects on the similarity measure, regardless of their magnitude. Accordingly, the pattern intensity is less sensitive to image artifacts.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method in image-guided surgery for determining the measure of similarity of a first image of an object and a second image of said object, the method comprising:
   a. forming a difference image by subtracting the corresponding pixel values of the second image from each pixel value of the first image;
      wherein said first image is an x-ray image of said object generated in near real time, and said second image is a DRR (digitally reconstructed radiograph) synthesized from previously generated 3D scan data of said object; and
   b. forming a pattern intensity function by summing asymptotic functions of the gradients of said difference image over all the pixels within a neighborhood R;
      wherein said neighborhood R is defined so that said gradients of said difference image can be considered in at least four directions.

2. A method in accordance with claim 1, wherein said pattern intensity function is an asymptotic function of the gradients of said difference image.

3. A method in accordance with claim 1, wherein said first and second images, and said difference image, are digital images.

4. A method in accordance with claim 1, wherein said first and second images are discretized images respectively characterized by a first and a second 2D (two-dimensional) array of pixel values; and
   wherein said difference image is a discretized image characterized by a third 2D array of pixel values.

5. A method in accordance with claim 4, wherein each pixel value of an image is a number representative of the intensity of said image at a corresponding 2D array element.

6. A method in accordance with claim 4, wherein the number of rows of said first array is equal to the number of rows of said second array and said third array, and the number of columns of said first array is equal to the number of columns of said second array and said third array.

7. A method in accordance with claim 4, wherein the number of rows and columns of said first and second arrays is about 512.

8. A method in accordance with claim 4,
wherein the pixel value for each image represents the intensity of said image, and
wherein the pixel value at the i-th row and j-th column of said third array of pixel values for said difference image is given by:

$$I_{dif}(i,j)=I_{Live}(i,j)-I_{DRR}(i,j),$$

wherein $I_{Live}(i,j)$ represents the (i,j)-th pixel value of a real-time x-ray image of said object, and $I_{DRR}(i,j)$ represents the (i,j)th pixel value of a digitally reconstructed image of said object synthesized from previously generated 3D scan data of said object.

9. A method in accordance with claim 1, wherein said x-ray image of said target is obtained by transmitting through said target an imaging beam having a known intensity and a known position and angle relative to said target, and wherein said 2D DRR (digitally reconstructed radiographs) representing the radiographic image of said target that would be obtained with said imaging beam at said known intensity, position and angle, if said target were positioned in accordance with said 3D scan data.

10. A method in accordance with claim 1,
wherein said pattern intensity function is characterized by a mathematical formulation given by:

$$\sum_{i,j}\sum_{k,l\in R}\frac{\sigma^2}{\sigma^2 + (I_{dif}(i,j) - I_{dif}(i+k, j+l))^2},$$

where $I_{dif}(i,j)$ represents the array of pixel values for said difference image, where σ is a weighting constant for weighting said function, and where R is a neighborhood defined around the pixel (i,j) as a center point.

11. A method in accordance with claim 10, wherein σ is from about 4 to about 16.

12. A method in accordance with claim 1, wherein said at least four directions comprise:
 a. a substantially horizontal direction;
 b. a substantially vertical direction;
 c. a diagonal direction of about 45 degrees; and
 d. a diagonal direction of about −45 degrees.

13. A method in accordance with claim 12, Wherein the result of the sampling of said pattern intensity in said neighborhood R, the pattern intensity function is given by:

$$\sum_{i,j}\frac{\sigma^2}{\sigma^2 + (I_{dif}(i,j) - I_{dif}(i, j-1))^2} + \sum_{i,j}\frac{\sigma^2}{\sigma^2 + (I_{dif}(i,j) - I_{dif}(i-1, j))^2} +$$

$$\sum_{i,j}\frac{\sigma^2}{\sigma^2 + (I_{dif}(i,j) - I_{dif}(i-1, j-1))^2} + \sum_{i,j}\frac{\sigma^2}{\sigma^2 + (I_{dif}(i,j) - I_{dif}(i-1, j+1))^2}.$$

14. A method in accordance with claim 1, wherein said 3D scan data comprise at least one of CT scan data, MRI scan data, ultrasound scan data, and PET (positron emission tomography) data.

15. A system for determining the measure of similarity of a 2D x-ray image of an object and a 2D DRR of said object generated from previously obtained 3D scan data, said x-ray image and said DRR being discretized images characterized by a first and second 2D array of pixel values, the system comprising:
 a. means for generating 3D scan data of said object;
 b. an x-ray source for generating at least one imaging beam;
 c. imaging means for generating a 2D radiographic image of said object in near real time, by directing said imaging beam towards and through said object from a known location and angle and at a known intensity, and detecting said imaging beam after said beam has passed through said object;
 d. a controller, including:
  i) software for generating a set of 2D DRR images of said object, using said 3D scan data and said known location, angle, and intensity of said imaging beam; and
  ii) software for determining the measure of similarity between said 2D x-ray image and said 2D DRR, by subtracting each pixel value of said second image from a corresponding pixel value of said first image to form a difference image, by adding the asymptotic functions of the gradients of the difference image over all the pixels within a neighborhood R;
 wherein said pattern intensity function is an asymptotic function of the gradients of said difference image; and
 wherein said neighborhood R is defined so that said gradients of said difference image can be considered in at least four directions.

16. A system in accordance with claim 15, wherein said at least four directions comprise:
 a. a substantially horizontal direction;
 b. a substantially vertical direction;
 c. a diagonal direction of about 45 degrees; and
 d. a diagonal direction of about −45 degrees.

17. A system in accordance with claim 15,
wherein said pattern intensity function is given by:

$$\sum_{i,j}\sum_{k,l\in R}\frac{\sigma^2}{\sigma^2 + (I_{dif}(i,j) - I_{dif}(i+k, j+l))^2},$$

where $I_{dif}(i,j)$ represents the array of pixel values for said difference image, where σ is a weighting constant, and wherein said neighborhood R uses the pixel (i,j) as a center point.

* * * * *